United States Patent
Giori et al.

(10) Patent No.: US 10,251,846 B2
(45) Date of Patent: Apr. 9, 2019

(54) ORAL COMBINATION FOR THE PREVENTION AND TREATMENT OF BLADDER, PELVIC AND UROGENITAL APPARATUS PATHOLOGIES

(71) Applicant: Altergon S.A., Lugano (CH)

(72) Inventors: Andrea Maria Giori, Lugano (CH); Enzo Lucherini, Lugano (CH)

(73) Assignee: Altergon S.A., Lugano (CH)

( * ) Notice: Subject to any disclaimer, the term of this patent is extended or adjusted under 35 U.S.C. 154(b) by 0 days.

(21) Appl. No.: 14/762,025

(22) PCT Filed: Jan. 20, 2014

(86) PCT No.: PCT/EP2014/000138
§ 371 (c)(1),
(2) Date: Jul. 20, 2015

(87) PCT Pub. No.: WO2014/111268
PCT Pub. Date: Jul. 24, 2014

(65) Prior Publication Data
US 2015/0320789 A1 Nov. 12, 2015

(30) Foreign Application Priority Data

Jan. 21, 2013 (IT) .............................. MI2013A0075

(51) Int. Cl.

| | | |
|---|---|---|
| A61K 31/352 | (2006.01) | |
| A61K 31/728 | (2006.01) | |
| A61K 31/12 | (2006.01) | |
| A61K 9/00 | (2006.01) | |
| A61K 9/48 | (2006.01) | |
| A61K 31/737 | (2006.01) | |
| A23L 33/10 | (2016.01) | |

(52) U.S. Cl.
CPC .............. *A61K 31/12* (2013.01); *A23L 33/10* (2016.08); *A61K 9/0053* (2013.01); *A61K 9/4825* (2013.01); *A61K 31/352* (2013.01); *A61K 31/728* (2013.01); *A61K 31/737* (2013.01); *A23V 2002/00* (2013.01)

(58) Field of Classification Search
CPC .... A61K 31/12; A61K 31/352; A61K 31/728; A61K 31/737; A61K 9/0053; A61K 9/4825; A61K 2300/00
USPC .......................................................... 514/54
See application file for complete search history.

(56) References Cited

U.S. PATENT DOCUMENTS

| | | | |
|---|---|---|---|
| 2001/0051184 A1* | 12/2001 | Heng ................... | A61K 9/0014 424/461 |
| 2003/0175332 A1 | 9/2003 | Brown et al. | |
| 2005/0220912 A1* | 10/2005 | Theoharides ........ | A61K 31/138 424/771 |
| 2006/0040894 A1* | 2/2006 | Hunter ................... | A61K 31/19 514/54 |
| 2009/0181924 A1 | 7/2009 | Zoppetti | |

OTHER PUBLICATIONS

Trisha Gura, Science, Nov. 1997, 278(5340), 1041-42.*
Girish K S et al: "Inhibition of Naja naja Venom Hyaluronidase by Plant-Derived Bioactive Components and Polysaccharides", Biochemistry (Moscow), Kluwer Academic Publishers-Plenum Publishers, NE, vol. 70, No. 8, Aug. 2005 (Aug. 2005), pp. 948-952.
Tolino A et al: "Treatment of vaginal distrophic and inflammatory pathologies with a new product containing 10 mg of jaluronic acid, 18.beta.-glicirretic acid and natural compounds (Vaginol(R))", Giornale Italiano Di Ostetricia E Ginecologia, Rome, IT, vol. 28, No. 9, Sep. 2006 (Sep. 2006), pp. 442-447.
International Search Report from PCT/EP2014/000138 dated Mar. 11, 2014.

* cited by examiner

*Primary Examiner* — Ganapathy Krishnan
(74) *Attorney, Agent, or Firm* — Fox Rothschild LLP

(57) ABSTRACT

The invention describes a pharmaceutical association of active ingredients comprising: curcumin, quercetin, chondroitin sulfate and hyaluronic acid, used for the prevention or treatment of bladder, pelvic and urogenital apparatus pathologies.

6 Claims, 2 Drawing Sheets

ORAL COMBINATION FOR THE PREVENTION AND TREATMENT OF BLADDER, PELVIC AND UROGENITAL APPARATUS PATHOLOGIES

CROSS-REFERENCE TO RELATED APPLICATIONS

This application is a § 371 national stage entry of International Application No. PCT/EP2014/000138 filed Jan. 20, 2014, which claims priority to Italian Application No. MI2013A000075 filed Jan. 21, 2013, both of which are hereby incorporated by reference in their entireties.

STATE OF THE ART

The bladder is a hollow muscular organ, located in the pelvis, the function of which is to accumulate the urine produced by the kidneys. Urine reaches the bladder through the ureters and is expelled outside through the urethra.

The epithelial tissue, or urothelium, coats the inside of the bladder and performs the important function of making the wall of the bladder impermeable, preventing the toxic substances contained in the urine from being reabsorbed, making the action of the kidneys pointless and causing damage to the underlying tissues.

The impermeability of the urothelium is ensured by the cellular structure of the epithelium itself, which also ensures its stretchability. The upper layer of the urothelium, i.e. that most directly in contact with urine, is formed from umbrella-like cells capable of modifying their shape based on the volume of liquid contained in the bladder.

Moreover, a crucial role in maintaining correct impermeability is performed by the mucus layer that uniformly covers the mucosa. This mucus mainly consists of polysaccharides, glycosaminoglycans (GAG), the polyanionic structure of which prevents the diffusion of toxic molecules from urine to the epithelium below. GAGs isolated from the urothelial mucus include hyaluronic acid, chondroitin sulfate, dermatan sulfate and keratan sulfate.

Dysfunctions compromising the impermeability of the urothelium are at the origin of many of the pathologies of the bladder and of the urogenital apparatus (see for example Parsons *"The role of a leaky epithelium and potassium in the generation of bladder symptoms in interstitial cystitis/overactive bladder, urethral syndrome, prostatitis and gynaecological chronic pelvic pain"* BJU Intern. 107, 370-375, 2010; Hanno P M *"Painful bladder syndrome/interstitial cystitis and related disorders"* Campbell-Walsh Urology edition, ed. 9, chap. 10. Elsevier, Mosby, Saunders; 2007.).

The alteration and reduction of the mucus layer results in greater vulnerability to infection and direct contact between the toxic metabolites present in urine and the urothelial cells. After being damaged, they can partially lose their barrier function, allowing toxins to penetrate into the muscle tissue.

A direct consequence of this phenomenon is the state of inflammation and irritation typical of pathologies like haemorrhagic cystitis, nonbacterial cystitis and acute bladder pain syndrome. Indeed, these are pathologies that are accompanied by damage to the bladder wall and in particular to the epithelial mucosa and to the mucous layer. In the most serious cases, ulcers may occur, as reported in in some forms of interstitial cystitis.

Moreover, there is clinical evidence linking the reduction of urothelial impermeability, both at mucus level and umbrella cell level, to bacterial infections of the urinary apparatus, bladder damage from chemotherapy with cyclophosphamide, endometriosis, pelvic pain, vulvodynia, urethritis, prostatitis and some forms of chronic neuropathic pain. In particular, also the epithelium of the urethra is protected by a GAG-based mucus. An epithelial dysfunction of the urinary tracts can thus lead to similar damage to the bladder and urethra.

The penetration of toxins in the urothelium, caused by a reduction of the barrier effect, can also be one of the factors triggering an abnormal cell proliferation, i.e. the appearance of tumour forms.

The bladder tumour, in its different forms, is overall the seventh most frequent carcinoma in the male population. Most carcinomas of the bladder involve the urothelium, like in the case of transition cell carcinoma, representing 95% of bladder tumours. For these forms of carcinoma, the risk of recurrence is very high, even reaching values of 46% at 3 months from the first surgical removal treatment and 80% at 5 years. Therefore, these are tumour forms that require continuous post-operatory check-ups and repeated treatments over time, leading to the highest treatment costs among all carcinomas (see for example van Rhijn et al. *"Recurrence and progression of disease in Non-Muscle-Invasive Bladder Cancer: from epidemiology to treatment strategy"* Europ. Urology 56, 430-442, 2009).

The reduction of the number of post-operatory recurrences is thus an important objective of clinical and pharmacological research.

The treatment of tumour pathologies of the bladder or abdomen with radiotherapy is itself responsible for urothelial damages, with the appearance of cystitis from radiotherapy. Also in this case, restoring the bladder mucosa and the mucus layer, i.e. recovering the barrier function is a clear therapeutic target.

Among the main therapies investigated for the treatment of pathologies like interstitial cystitis and chronic bladder pain there are various preparations for intra-bladder instillation. Examples of such preparations are solutions of silver nitrate, dimethylsulfoxide, solutions of neurotoxins (like resiniferatoxin and botulin toxin of type A), solutions of phospholipids in liposomal form and exogenous GAG solutions. The most popular among them is heparin, although hyaluronic acid and chondroitin sulfate have also been used. In particular, patent application US 2009/0181924, to the same Applicant, claims the intra-bladder use of aqueous solutions containing mixtures of hyaluronic acid and chondroitin sulfate.

In all of the cases listed, the method of administration is intra-bladder, with all the limitations that this approach involves. Although on the one hand for some preparations there can be good effectiveness of the treatment, on the other hand the technique is invasive, requires the use of catheters and can only be applied by a specialist, in some cases under anaesthetic treatment (e.g. with silver nitrate).

In order to overcome the limitations of intra-bladder therapy, many oral preparations have been tested, but often with not fully satisfactory results. Moreover, oral therapy is based on the use of drugs such as tricyclic antidepressants (in particular amitriptyline) or antihistaminic agents (like hydroxyzine) that have substantial side-effects and make long-term therapy unadvisable.

Oral supplementation of exogenous GAGs, performed in an attempt to influence the mucosal layer of the urothelium, up to now has proven only partially effective. Sodium pentosan polysulfate, a synthetic GAG similar to heparin, is the only oral drug approved in the USA for the treatment of interstitial cystitis, yet it requires long treatment times to afford the first benefits (from 3 to 6 months) and its therapeutic validity is still disputed (Hanno 2007, Op. cit.)

Therefore the need is still unmet for compositions that, being administered in a less invasive way than intra-bladder, are able to preserve or repair the GAGs-based urothelium and mucous layer, maintaining or recovering suitable impermeability of the bladder membrane. Such compositions should be easily tolerated, easy to administer, and compatible with chronic administration regimes, avoiding recourse to heavy pharmacological therapies.

Further unmet is the need for effective, easy to apply and non-invasive therapies for treating of bladder pathologies like haemorrhagic cystitis, nonbacterial cystitis, cystitis from radiotherapy, damage from chemotherapy with cyclophosphamide, interstitial cystitis and acute bladder pain and other pathologies linked to urothelial hyperpermeability, such as endometriosis, pelvic pain, vulvodynia, urethritis, prostatitis and some forms of chronic neuropathic pain, all these pathologies involving a damage to bladder/urethral wall, epithelial mucosa and mucus layer.

SUMMARY

It has now surprisingly been discovered that an association of curcumin, quercetin, hyaluronic acid and chondroitin sulfate, administered orally, is able to act positively on the urothelial mucus layer, improving its uniformity and thickness. The present oral treatment overcomes the problems and limitations of the non-oral therapies currently applied, involves substances of proven safe use, and ensures low costs and good compliance of the patient.

DETAILED DESCRIPTION OF THE INVENTION

Figure 1:
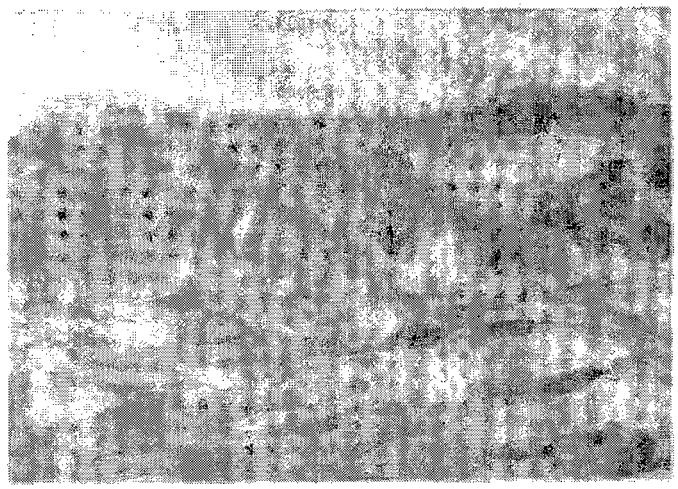
FIG. 1: histological examination of the urothelium taken after treatment with the oral composition of the invention (staining with EE)

The term "curcumin" refers without distinction to the product obtained from natural sources, or its synthetic equivalent, in any of its tautomeric ketonic or enolic forms, or a salt or derivative thereof like for example desmethoxycurcumin or bis-desmethoxycurcumin, or mixtures thereof; an example of such mixtures is that of extracts from turmeric rhizomes (*Curcuma longa*).

The term "quercetin" refers without distinction to the product as obtained from natural sources, or its synthetic equivalent, in any of its tautomeric ketonic or enolic forms, or a salt or derivative thereof such as a conjugate, for example quercetin-3-O-sulfate, or it can be in the form of aglycone of a glycoside, e.g. rutin or quercitrin.

The term "chondroitin sulfate", as known, identifies a glycosaminoglycan sulfate made of units of N-acetylgalactosamine and glucuronic acid, in variable number, and with sulfated oxydryls variable in amount and/or position; the term includes for example chondroitin-4-sulfate, chondroitin-6-sulfate, chondroitin-2,6-sulfate, chondroitin-4,6-sulfate and their mixtures, etc.; the term also includes the relative salts and derivatives.

The term "hyaluronic acid", as known, identifies a polymer of glucuronic acid and N-acetylglucosamine, with a molecular weight generally comprised between 5 KDa and 20,000 KDa; preferably the molecular weight is comprised between 50 KDa and 3,000 KDa; the term includes the relative salts and derivatives.

The term "association" refers to the preparation and/or combined use of the associated ingredients; the combined use can be simultaneous or non-simultaneous; simultaneous use involves administration of all of the active ingredients object of the association at the same time, and a suitable formulation of them; non-simultaneous use foresees administration of all of the active ingredients forming part of the association, where one or more of them are formulated and/or administered separately from the others; such use remains subject to suitable administration instructions, such that the patient obtains the combined effect of all of the active ingredients object of the association.

The association of curcumin, quercetin, chondroitinsulfate and hyaluronic acid can be administered as a physical mixture of the four active ingredients, or as a mixture of two or three of them in association with the remaining active ingredient(s), or through separate dosage units for all the active ingredients; in any case, the separate administrations are carried out within a therapeutic framework, in particular according to times and doses suitable for combined action, to obtain closely related or overlapping time plasma curves of the thus associated active ingredients.

The active ingredients that make up the association can be administered in variable amounts and proportions according to the patient and the type of pathology and how serious it is. Preferably, the active ingredients are used in the following percentages by weight: curcumin from 10 to 30%; quercetin from 20 to 40%; chondroitinsulfate from 20 to 40%; hyaluronic acid from 2 to 20%; said percentages are calculated with respect to the total of curcumin, quercetin, chondroitinsulfate, hyaluronic acid, and they also remain valid where the aforementioned drugs are mixed with other excipients and/or other active ingredients.

When formulated as a single dosage unit, the present association preferably comprises a total amount of curcumin, quercetin, chondroitin sulfate and hyaluronic acid, comprised between 300 and 3000 mg, more preferably between 400 and 1500 mg.

A preferred standard dosage unit comprises: 100 mg curcumin, 200 mg quercetin, 200 mg chondroitin sulfate and 20 mg hyaluronic acid or a sodium salt thereof.

The present treatment can be carried out extemporaneously or repeated over time; more marked effects are obtained through repeated daily administration: the duration of such treatment cycles can be, for example, 5, 30, 60, 90, 120, 150, 180 days, or it can have a duration comprised in any range defined by the aforementioned numbers of days.

The treatment is applicable to all pathologies that involve an alteration of the bladder, urethra, pelvis and urogenitals; it is particularly aimed at protecting and/or restoring the mucus state of the mucosae involved, and at protecting said mucosae from inflammation. Examples of pathologies that can be treated with the present association are: cystitis, such as interstitial cystitis, haemorrhagic cystitis, nonbacterial cystitis, cystitis from radiotherapy; urethritis; damage from radiotherapy or chemotherapy, for example from cyclophosphamide; infections, such as urogenital infection; painful syndromes, such as acute bladder pain, pelvic pain, chronic neuropathic pain; pathologies involving the genital organs: endometriosis, vulvodynia, prostatitis; neoplasia, e.g. bladder tumours such as transition cell carcinoma.

The invention comprises the association of the aforementioned active ingredients for use in the treatment or prevention of the pathologies indicated above.

The invention also includes the use of the aforementioned ingredients in association with each other, in the preparation of a drug that can be used for treating the aforementioned pathologies.

The invention also extends to a method for the treatment of the aforementioned pathologies, characterised by administering the association of active ingredients defined earlier to a patient in need thereof.

Administration preferably takes place orally, obtaining the advantage of a simpler method of administration than the intra-bladder method conventionally used. In the case of oral administration, all of the suitable pharmaceutical forms known in the state of the art can be used: in particular tablets, granulates, powders, capsules, microcapsules, pellets, films, gels, solutions, suspensions, etc. Among capsules, soft gelatine ones are preferred, in the presence of suitable pharmaceutically acceptable carriers.

The present invention therefore includes pharmaceutical or nutritional compositions comprising the four active ingredients mentioned above, as such or in mixture with excipients for pharmaceutical or food use. Among possible excipients we can quote diluents or fillers, disintegrants, emulsifiers, humectants, gelifiers, thickeners, lubricants, preservatives, flavourings, dyes, etc. Examples of such excipients are readily available from pharmaceutical technology manuals.

The nutritional compositions can be formulated for example as integrators, in forms of direct administration, the same as pharmaceutical ones, or they can be supplied as medicated food supports where the aforementioned active ingredients, possibly carried with excipients, are dispersed inside a food support.

All of the compositions can contain, in addition to the active ingredients characteristic of the invention, further active ingredients, in particular those used for the treatment of the illnesses indicated above; such further active ingredients are optional, i.e. their presence is not essential since the therapeutic effect is ensured by the association of the active ingredients object of the invention.

The invention also include a process for preparing the aforementioned compositions, characterised by associating together: curcumin, quercetin, hyaluronic acid, chondroitin sulfate, pharmaceutical or food excipients, and/or a food support. The mixing and formulation techniques are selected from those currently known.

The invention also concerns a kit suitable for the administration of the present association of active ingredients. The kit comprises a number of independent dosage units such as to allow a patient a combined, not necessarily simultaneous, administration of curcumin, quercetin, hyaluronic acid, chondroitin sulfate. The kit can comprise separate dosage units for the administration of each active ingredient; or it can comprise dosage units containing mixtures of a few of the aforementioned active ingredients, associated with dosage units containing the remaining active ingredients to complete the association. Such dosage units can be present in multiple number, to administer the association repeatedly during a treatment cycle of many days, e.g. in the ranges of days indicated above. The kit is preferably equipped with suitable instructions to carry out the combined administration of the active ingredients in object.

The invention will now be described in a non-limiting way by the following examples.

EXAMPLES

Patients suffering from transition cell bladder carcinoma were subjected to oral treatment with a combination of curcumin, quercetin, hyaluronic acid and chondroitin sulfate; after surgical removal of the tumour, the effect of the oral treatment on the layer of GAGs covering the urothelium, on the urothelium itself and on the tumour recurrences were tested. The results obtained prove the effectiveness of the treatment object of this invention.

Example 1

Some soft gelatine capsules weighing 1.8 g each were prepared. Each capsule contains the components listed in table 1 in the amounts shown:

TABLE 1

| | Ingredient | mg per capsule |
|---|---|---|
| Filler | chondroitin sulfate | 200 |
| | quercetin | 200 |
| | curcumin | 100 |
| | soy lecithin | 200 |
| | hyaluronic acid | 20 |
| | medium-chain triglycerides | 500 |
| | propylene glycol monolaurate | 120 |
| Shell | gelatine | 320 |
| | Glycerol | 162 |
| | water | 270 |

Example 2

9 patients (4 female and 5 male—average age 67.2 years) suffering from superficial transition cell bladder carcinoma, of high and low degree (Ta or Ti) and tumour diameter of less than 3 cm were selected. The selected subjects were subjected to transurethral bladder resection of the visible lesions and to simultaneous biopsy of a part of the bladder mucosa not affected by tumour, used as control. Both of the tissues thus recovered were subjected to microscope examination, using staining with hematoxylin-eosin (EE), for the examination of cell morphology, and with PAS (Periodic Acid-Schiff) for the examination of the glycoproteins and of the polysaccharides (in particular GAGs).

Figure 2:
FIG. 2: histological examination of a tumour neoplasm (staining with PAS)
Figure 3:
FIG. 3: histological examination of the healthy urothelium taken at the site of transurethral resection intervention (staining with PAS); (A)=surface layer of GAGs-containing mucus.

The results are shown in FIGS. 2 and 3, respectively for the urothelium suffering from tumour and for the healthy one. FIG. 2 clearly shows the depletion of the surface mucus layer after the tumour; vice-versa, in FIG. 3 (healthy tissue) such a layer is still very clear. This thus confirms the alteration of the metabolism of the glycoproteins in the case of tumour neoplasms.

After transurethral bladder resection, all of the subjects involved started to take two soft gelatine capsules/day of the composition described in example 1. The treatment lasted three months. No other treatments were carried out.

No side-effect of the oral treatment was reported by the patients at the end of the three months administration.

At the end of the treatment all of the patients were subjected to a second control biopsy, to check the progress of the illness and the effects of the treatment. Indeed, clinical literature (van Rhijn 2009, Op. cit.) indicates a risk of recurrence after transurethral resection of up to 46%.

Surprisingly, the results of the second biopsy show the complete absence of bladder neoplasms in all of the subjects examined. In particular, the microscope examination of the mucosal tissues after staining with EE did not show any sign of dysplasia, nor the presence of tumour cells (FIG. 1); there is thus a complete absence of tumour recurrence, contrary to what is normally expected.

Figure 4:
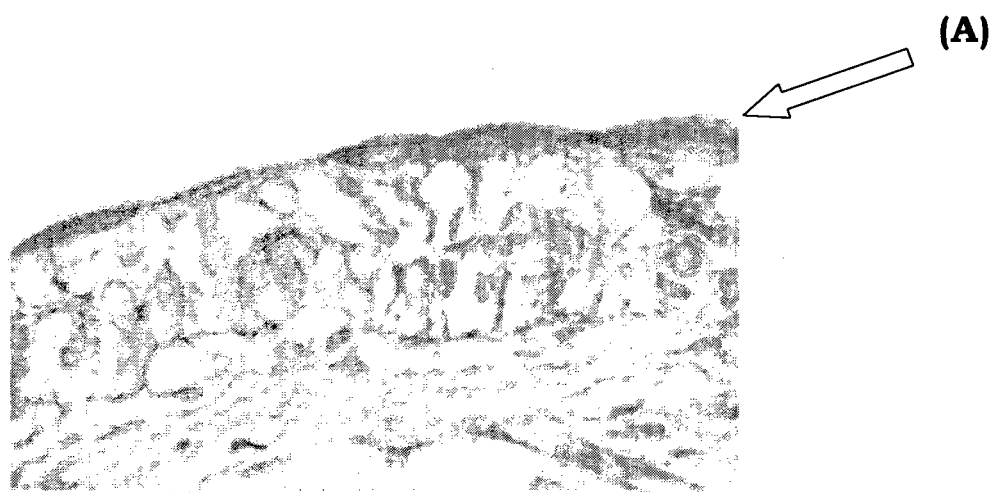
FIG. 4: histological examination of the healthy urothelium taken at the site of control biopsy, after treatment with the oral composition of the invention (colouring with PAS); (A)=surface layer of GAGs-containing mucus

Moreover, the histological examination of the sections of urothelium thus obtained indicates, after staining with PAS that the protective layer of GAGs on the tumour tissues (FIG. 4) has been restored. Such a layer is also bigger, more even and well distributed than what was initially found on the healthy tissue at the time of the first biopsy (FIG. 3).

The treatment is thus effective not only in restoring the physiological mucosal layer existing before the pathological event, but also in further improving its quality and the relative protective properties.

There is thus experimental confirmation of the effectiveness of the oral combination object of this invention in maintaining and improving the protective barrier of the urothelium, ensuring low permeability of the mucosa and low contact with the toxic substances contained in urine. It is also reasonable to suppose that this result is directly involved in the absence of tumour recurrences found in the clinical trial carried out.

The invention claimed is:

1. A method for treating bladder, pelvic or urogenital apparatus pathologies, comprising by orally administering, to a patient in need thereof, a pharmaceutical or nutritional association comprising the active ingredients: curcumin, quercetin, chondroitin sulfate and hyaluronic acid, wherein said pathologies are selected from the group consisting of cystitis, endometriosis, prostatitis, urethritis, pain syndrome, infections, bladder tumors and transition cells carcinoma, wherein said active ingredients are present in the following amounts by weight, with respect to the total of said active ingredients:
   10-30% curcumin;
   20-40% quercetin;
   20-40% chondroitin sulfate;
   2-20% hyaluronic acid.

2. The method in accordance with claim 1, wherein said cystitis is selected from the group consisting of: interstitial cystitis, hemorrhagic cystitis, nonbacterial cystitis and cystitis from radiotherapy; said infection is urogenital infection; said pain is selected from the group consisting of acute bladder pain, pelvic pain and chronic neuropathic pain.

3. The method in accordance with claim 1, comprising, per dosage unit, an overall quantity of curcumin, quercetin, chondroitin sulfate and hyaluronic acid, between 300 to 3000 mg.

4. The method in accordance with claim 1, wherein the association is administered orally.

5. The method in accordance with the claim 4, wherein the association is administered daily for a period comprised between 5 and 180 days.

6. A method for treating bladder, pelvic or urogenital apparatus pathologies, comprising orally administering, to a patient in need thereof, a pharmaceutical or nutritional association consisting essentially of the active ingredients: curcumin, quercetin, chondroitin sulfate and hyaluronic acid, wherein said pathologies are selected from the group consisting of: cystitis, endometriosis, prostatitis, urethritis, pain syndrome, infections, bladder tumors and transition cells carcinoma, wherein said active ingredients are present in the following amounts by weight, with respect to the total of said active ingredients:
   10-30% curcumin;
   20-40% quercetin;
   20-40% chondroitin sulfate;
   2-20% hyaluronic acid.

* * * * *